United States Patent [19]

Dzbanovsky et al.

[11] Patent Number: 5,093,106
[45] Date of Patent: Mar. 3, 1992

[54] METHOD FOR CONTRASTING MALIGNANT NEOPLASMS USING FLUORESCEIN AND A SUGAR

[76] Inventors: Nikolai N. Dzbanovsky, ulitsa V.Ulbrikhta, 8, kv. 95.; Viktor I. Polsachev, Izmailovsky prospekt, 123/I, kv. 29; Elena V. Potemkina, Frunzenskaya naberezhnaya, 8 kv. 26; Alexandr T. Rakhimov, Rostovskaya naberezhnaya, I, kv. 95; Leonid B. Rubin, Lomonosovsky prospekt, 14, kv. 499; Alexandr S. Osipov, Mosfilmovskaya ulitsa, 32, kv. 42, all of Moscow, U.S.S.R.

[21] Appl. No.: 485,785
[22] Filed: Feb. 23, 1990

Related U.S. Application Data

[63] Continuation of Ser. No. 255,120, Oct. 7, 1988, abandoned.

[30] Foreign Application Priority Data

Oct. 15, 1987 [SU] U.S.S.R. ............................. 4313068

[51] Int. Cl.$^5$ .................... G01N 33/15; G01N 31/00; A61K 31/35
[52] U.S. Cl. ........................................ 424/7.1; 424/9; 514/455
[58] Field of Search ...................... 424/7.1, 9; 514/455

[56] References Cited

U.S. PATENT DOCUMENTS 4,401,755  8/1983  Weaver .................................. 435/34
4,820,505  4/1989  Ginsberg et al. ....................... 424/9
4,912,208  3/1990  Fiechtner et al. ..................... 536/53
4,913,908  4/1990  Couvreur et al. ................... 424/501

OTHER PUBLICATIONS

"Cancer Detection and Therapy . . ." by Figge, et al., Proceedings of the Society for Experimental Biology and Medicine, vol. 68, No. 3, Jul.-Aug., 1948, pp. 640 and 641.
"Using a Fluorescein in Operation . . ." by Mostovoi, The Journal of Ears, Noses & Throats Diseases, No. 4, 1961, pp. 34-36.
"Glucose Administration Augments . . ." by Thomas, et al. Photochemistry and Photobiology, vol. 49, No. 3, 1989, pp. 241-247.
Science, The Scientists' Newsweekly (Jul. 1947) Moore, G. E., vol. 106, pp. 130-131.
Gastroenterology, vol. 41, No. 1, Klinger, J. et al., pp. 29-32, (1961).
"Cancer Detection & Therapy . . ." by Figge, et al., Proceedings of the Society for Experimental Biology & Medicine vol. 68, No. 3, Jul.-Aug., 1948, pp. 640-641.
"Using a Fluorescein in Operation . . ." by Mostovoi The Journal of Ears, Noses & Throats Diseases, No. 4, 1961, pp. 34-36.
"Glucose Administration Augments . . ." by Thomas, et al., Photochemistry & Photobiology, vol. 49, No. 3, 1989, pp. 241-247.

*Primary Examiner*—Glennon H. Hollrah
*Assistant Examiner*—Gary Hollinden
*Attorney, Agent, or Firm*—Burgess, Ryan and Wayne

[57] ABSTRACT

The present invention is used for diagnosis, including early diagnosis, of malignant growths, for assessment as of the extent of malignant infection, for determining of the required volume for surgical intervention, for finalizing diagnoses under clinical and dispensary conditions, for control during the process of treatment of malignant tumors, and for detection of post-operative relapses.

The contrasting composition according to the present invention is characterized in that, in addition to the contrasting composition, namely, fluorescein, or salts thereof, it comprises sugar.

10 Claims, No Drawings

METHOD FOR CONTRASTING MALIGNANT NEOPLASMS USING FLUORESCEIN AND A SUGAR

This application is a continuation, of application Ser. No. 255,120, filed 10/7/88, now abandoned.

FIELD OF THE INVENTION

This invention relates to the art of medicine and, more specifically, to oncology.

The best advantage may be derived from use of the present invention for diagnostics, including at an early stage, of malignant growths for assessment of the extent of malignant affection, for determining the required volume of surgical operations, for finalizing diagnoses under clinical and dispensary conditions, for control during treatment of malignant tumours, and for detection of post-operative relapses.

BACKGROUND OF THE INVENTION

At present, the problem of diagnostics of malignant neoplasms, especially at early stages, is of vital importance in oncology. In spite of an extensive use of histological analytical methods, great successes of ultrasonic and X-ray diagnostics, in spite of great progress achieved in endoscopic examination methods, as well as in X-ray and nuclear magnetic resonance (NMR) tomography, the sensitivity, accuracy and availability of these methods still remain inadequate. One of the promising trends for perfecting the diagnosis of malignant tumours resides in the use of contrasting agents capable of being selectively accumulated in such tumours. It is a well established fact, for instance, that malignant tumours accumulate some dyes at elevated concentrations as compared to healthy body tissues, and this fact is used for fluorescent diagnosis of tumours using the fluorescence characteristic of a dye accumulated therein.

Various compositions, such as, antibiotics of the tetracycline group, have been used as fluorescent contrasting agents. One of the diagnostic methods made it possible to detect stomach cancer at late IIIrd and IVth stages of the disease, however, with a degree of precision found insufficient for diagnostic purposes (Cf. I. Klinger, K. Katz. Gastroenterology, enterology, 1961, 41, 29-32). Use of endoscopic technique, in combination with fluorescent contrasting tetracycline agents (Cf. I. Ya. Barsky, G. V. Papayan, V. V. Shchedrunov and Yu. A. Glukhir Luminescent Analytical Methods in Medical and Biological Examinations, (a collection of publications), Riga, 1983, pp. 182-189) has also demonstrated poor reliability in diagnostics of tumours because of blurred contrast in which tetracycline accumulated in malignant tissues stands out as compared to healthy tissues.

Fluorescent contrasting using fluorescein as a dyeing agent has been used for detecting metastases into regional lymph nodes in larynx cancer (Cf. S. I. Mostovoy, J. of Disorders of the Ear, Nose and Throat, 1961, No. 4, pp. 34-36). It has been stated that not only cancer-affected lymph nodes, but also other body organs exhibited bright fluorescence, and this fact renders the method unsuitable for diagnostics. Some other authors also have arrived to the same conclusions (Cf. G. E. Moore, Science, 1977, 106, 130-131; F. H. I. Figge, G. S. Weiland, L. O. I. Manganiello, Proc. Soc. Exper. Biol. Med., 68, 640-641, 1948).

For contrasting malignant growths, attempts have been also made to use a contrasting agent containing, as a contrasting substance, fluorescin and used either in the form of a 20%-solution for intravenous administration in 2 to 5 ml doses, or in the form of 1 gr of powder washed down with soda water (Cf. Yu. N. Yefuni, Vestnik Otorhinolaryngology [in Russian], 1961, No. 2, pp. 11-15). The disadvantage of the latter contrasting agent lies in poor contrast offered by fluorescein accumulated in a malignant tissue as against a healthy tissue, whereby the accuracy of diagnostics is affected. The degree of contrast offered by fluorescein accumulated in a malignant tissue versus that accumulated in a normal body tissue has been assessed in terms of a ratio of the concentrations of fluorescein contained in these two types of tissues per gram of the tissue weight. According to the prior art, the reliability of fluorescent diagnostics of, e.g. malignant growths in the organs of the upper respiratory tract, was 30%. Accordingly, an inference may be arrived at that epithelial malignant tumours do not fluoresce, i.e. they do not accumulate fluorescein.

SUMMARY OF THE INVENTION

It is the object of the present invention to develop a composition for contrasting malignant neoplasms with a high degree of reliability of diagnostics. The above-formulated object has been unexpectedly attained due to using in a composition for contrasting, along with fluorescein, or with salts thereof, or with an anion thereof, additives in the form of sugars and/or disaccharides, vitamins and agents for blocking the permeability of cellular membranes. The mechanism of action of these additives in contact with fluorescein is by no means obvious a priori and resides in the following:

Fluorescein, being a fluorescent dyeing agent, has been since long used in biology and medicine. It is common knowledge that fluorescein does not penetrate into living cells, since its anion has a negative charge which prevents its passage through the cellular membrane. It has been established quite unexpectedly that addition of organic acids which are a product of cellular metabolism, to a fluorescein solution leads to the formation of a complex neutralizing the charge of the fluorescein anion and, as a result, fluorescein starts penetrating and accumulating in cells. This effect has been used in the present invention for carrying out fluorescent diagnostics. The main point is that the malignant cells exhibit respiration of glycolytic type which is characterized by a higher rate of carbohydrate consumption and an acidification of inter-tissue fluid due to ejection of organic acids as final respiration products. As has been shown experimentally, a lower acidity of the medium leads to proteinization of fluorescein and to its greater solubility in cellular membranes and, as a result, to a sharp increase in the fluorescein concentration within malignant cells. Preferably, glucose or fructose as monosaccharides, and saccharose as a disaccharide are used as carbohydrates, which is determined by the specific physiological particular features of a human organism, for instance, by the fact that a patient suffers from diabetes mellitus.

Additions of vitamins A (retinol), $B_1$ (thiamine), $B_2$ (riboflavin), $B_6$ (chloride pyridoxine), P (rutin), E (acetate tocopherol), C (ascorbic acid), PP (nicotinic acid) lead to an all-out stimulation of the metabolic processes required for active transfer of fluorescein to malignant cells, in particular, they intensify the glycolysis process.

Use of agent for blocking the permeability of cellular membranes, preferably antihistaminic preparations, such as 3-methyl-9-benzyl-1,2,3,4-tetrahydrocarboline-naphthalin-1,5-disulphonate, or 10-(2-dimethylaminopropyl)-phenothiazine hydrochloride, or N-dimethylaminoethyl-N-(parachlorobenzyl)-aminopyridine hydrochloride, or 1-methyl-2-[2-(alpha-methylparachlorobenzohydryloxy)-ethyl]-pyrromedine, or 4,9-dihydro-4-(1-methyl-4-piperidinyliden)-1-OH-benzo[4,5]cyclohepta[1,2]-thiophen-10-OH (hydrofumarate), or beta-dimethylaminoethylic ether benzohydrol hydrochloride, or chinuclidyl-3-diphenylcarbinol hydrochloride as aimed at reducing the speed of removal of fluorescein from malignant cells. The other effect of the membrane-permeability blocking agents is to increase the fluorescein concentration in malignant cells and, as a result, a deeper contrast offered by fluroescein built-up in a greater amount in malignant cells. Consequently, the above-mentioned additives have a dual purpose, namely, they increase the selective build-up of fluorescein in cells, and, at the same time, they reduce the speed at which fluorescein leaves the cells. It will be appreciated that the selectivity of this process conditioned by the specific features of metabolism in malignant cells, is expressed, on the whole, by a deeper contrast offered by fluorescein accumulated in malignant tissues as against healthy tissues.

DETAILED DESCRIPTION OF THE INVENTION

Taking in due consideration the individual specific features of human organisms, the composition in accordance with the present invention may be recommended for administration in the following alternative formulations, %% by weight:

| 1. Fluorescein or salts thereof | 0.1 to 80 |
|---|---|
| Sugar and/or disaccharide | 20 to 99.9 |

The preferable composition comprises, %% by weight:

| fluorescein or salts thereof | 10 |
|---|---|
| sugar and/or disaccharide | 90 |

TABLE 1

| Contrasting composition comprises, %% by weight | | | | Contrast offered by the composition in relative units |
|---|---|---|---|---|
| Fluorescein or salts thereof 1 | Glucose 2 | Fructose 3 | Saccharose 4 | 5 |
| Known composition for comparison | | | | |
| 100 | — | — | — | 1.5 |
| 20 | — | 80 | — | 5.0 |
| 1 | — | — | 99 | 8.5 |
| 0.1 | 99.9 | — | — | 12.0 |
| 3 | 50 | — | 47 | 8.0 |

| 2. Fluorescein or salts thereof | 1 to 90 wt. % |
|---|---|
| Vitamins | 10 to 99 wt. % |

The preferable composition comprises %% by weight:

| fluorescein or salts thereof | 50 |
|---|---|
| vitamins | 50 |

TABLE 2

| Contrasting composition comprises, %% by weight | | | | | | | | | Contrast in rel. units |
|---|---|---|---|---|---|---|---|---|---|
| Fluorescein or salts thereof | Vitamins | | | | | | | | |
| | B₁ | B₂ | B₆ | A | P | E | C | PP | |
| Known composition for comparison | | | | | | | | | |
| 100 | — | — | — | — | — | — | — | — | 1.5 |
| 90 | 2 | 1 | 2 | 0.2 | 2 | 1 | 1 | 0.8 | 3.0 |
| 50 | 3 | 1.5 | 3 | 0.5 | 3 | 1.5 | 30 | 7.5 | 6.5 |
| 10 | 5.4 | 2.7 | 5.4 | 0.9 | 5.4 | 2.7 | 54 | 13.5 | 5.0 |
| 10 | 5.4 | 2.7 | — | — | 5.4 | 2.7 | 60.3 | 13.5 | 4.5 |

| 3. Fluorescein or salts thereof | 20 to 90 wt. % |
|---|---|
| Agents for blocking the permeability of cellular membranes | 10 to 80 wt. % |

The preferable composition comprises, %% by weight:

| fluorescein or salts thereof | 80 |
|---|---|
| agents for blocking the permeability of cellular membranes | 20 |

TABLE 3

| Fluorescein or salts thereof | 3-methyl-9-benzyl-1,2,3,4-tetrahydrocarbolin of naphthalin-1,5-disulphonate | Contrast in rel. units |
|---|---|---|
| Known composition for comparison | | |
| 100 | — | 1.5 |
| 90 | 10 | 4.5 |
| 50 | 50 | 3.0 |
| 10 | 90 | 2.5 |

The contrasting composition in accordance with the present invention may also comprise other combinations of the above-disclosed components, the most preferred being the following complete make-up of the composition, %% by weight:

| Fluorescein or salts thereof | 0.1 to 79.6 |
|---|---|
| Sugar and/or disaccharide | 19.4 to 98.9 |
| Vitamins | 0.5 to 80 |
| Permeability-blocking agents | 0.5 to 80 |
| The preferable composition comprises, %% by weight: | |
| fluorescein or salts thereof | 15 |
| sugar and/or disaccharide | 70 |
| vitamins | 10 |
| permeability-blocking agents | 5 |

TABLE 4

| Fluorescein or salts thereof | Contrasting composition comprises, %% by weight | | | | | | | | | Contrast in relative units |
|---|---|---|---|---|---|---|---|---|---|---|
| | * | ** | *** | $B_1$ | $B_2$ | $B_6$ | C | A | **** | |
| Known composition for comparison | | | | | | | | | | |
| 100 | — | — | — | — | — | — | — | — | — | 1.5 |
| 10 | — | — | — | — | — | — | 60 | — | 30 | 5 |
| 10 | — | — | — | 5 | 5 | 10 | 20 | — | 50 | 6 |
| 5 | — | — | 50 | 5 | 5 | 5 | 25 | 5 | — | 10 |
| 0.1 | 98 | — | — | — | — | — | 1 | 0.4 | 0.5 | 12 |
| 1 | — | 35 | — | 10 | 10 | 10 | 10 | — | 24 | 18 |
| 25 | — | 35 | — | 5 | 5 | 5 | 15 | 5 | 5 | 20 |

Note:
*glucose;
**fructose;
***saccharose;
****3-methyl-3-benzyl-1,2,3,4-tetrahydrocarbolin naphthalin-1,5-disulphonate If one of the above-identified ingredients of the contrasting composition in accordance with the present invention is excluded from the formulation specified in Table 4, the contrast offered by the present composition built-up in malignant tumours becomes somewhat weaker, remaining, nevertheless, at a higher level than that attainable with its prior-art analogues (See Tables 1–4).

Of basic importance is the fact that it is the fluorescein anion that constitutes the active principle in the present contrasting composition. The fluorescein anion penetrates into the patient's blood and is transported through the body tissues to be built-up in malignant neoplasms. For this reason, the present contrasting composition according to the present invention contains either fluorescein, or the salts thereof with, preferably, alkali metals or ammonium. When fluorescein or its salts are found in an alkaline medium, they dissociate to liberate the fluorescein anion.

The composition for contrasting malignant growths according to the present invention may be administered into the patient's body in a number of ways, such as by intravenous injections, enterally or through the rectum. Other variants are also possible, e.g. vitamins and carbohydrates are administered enterally, while fluorescein or its salts are administered intravenously.

The individual ingredients of the present contrasting composition may be used either in the form of a single solution, or as a powder, or as a plurality of individual solutions, or in solid state.

Used as a solvent for the present contrasting composition, either on the whole or for its individual ingredients, may be water or a 5- to 30%-aqueous solution of ethyl alcohol. Once the solution of the present contrasting composition is prepared, it is possible to adjust its optimum acidity by additions of salts and acids and also flavour additives.

A solvent may be used either jointly with the present contrasting composition (the latter being in dissolved form), or separately (the composition in pulverized form plus a solvent).

The assessment of the ability of fluorescein or its salts to be accumulated in malignant cells and tumours has been carried out on cellular cultures He-La, 3T3, IG-fibroregion, cultivated by the standard techniques. Fluorescein or its salts, along with the other ingredients of the present contrasting composition, have been added to the cellular culture, incubated for a few hours, followed by isolating a cellular fraction and washing it. The dye concentration was determined in the cells using chromatographic and fluorescent analytical methods.

In experiments on laboratory animals, use has been made of mice (a linear breed, CBA, C-57 Black and BALB-C) affected with cross-linked tumours of uterine neck cancer, Lewis and colon cancer, respectively. Upon expiration of a certain lapse of time after administration of fluorescein or its salts, along with the other above-identified ingredients, the animals have been anesthesized and killed to determine the dye concentration in the malignant and healthy tissues. The degree of contrast offered by the present composition was expressed in terms of a ratio of the dye concentration in a malignant tissue to that in a healthy tissue.

Laparoscopic examinations have demonstrated that fluorescein or its salts are accumulated in an ascitic fluid. It means that this fluid may be detected in very small amounts. Consequently, it becomes possible to detect the presence of malignant, visually undetectable, deeply embedded metastases in internal organs, such as liver, transperitoneal region, spleen, etc. This fact considerably expands the diagnostic potentialities of the laparoscopic technique.

Tables 1 to 4 report the results of experimental work on mice belonging to the CBA breed, affected with uterine neck cancer inoculated to the hip. These Tables also report data on the degree of contrast offered by fluorescein accumulated in malignant tissues as against normal surrounding tissues, depending on the present contrasting composition.

Malignant elements present in blood accumulate fluorescein or its salts, and they may be detected by their fluorescent contrast under a microscope.

The study of the localization of fluorescein in the body tissues has been started upon expiration of a certain lapse of time after administration of the present composition, since during this lapse of time, as shown by our experience, the dye has sufficient time, in the first place, to be uniformly distributed throughout all the tissues of the body and, in the second place, to get accumulated in malignant growths. Removal of the composition through the liver and kidneys starts practically immediately after administration of the present composition and, upon expiration of a specific lapse of time characteristic of exact localization, type and size of a malignant tumour, an elevated concentration of fluorescein or of its salts is detected in the tumour. Detection of the localization of fluorescein was conducted by the fluorescent analysis. The tissues having an elevated or a lower fluorescein concentrations have been subjected to a histological analysis for a final diagnosis as to their malignant nature.

It has been established that the reliability of diagnostics of malignant processes based on the detection of fluorescence of fluorescein accumulated in the body tissues as compared to the conventional histological analysis of tissue samples taken by biopsy accounts for 75 to 90%, depending on the localization of a tumour.

Identical results for the percentage of reliability of the fluorescent diagnostics have been obtained in clinical tests during which, all in all, 350 patients suffering from cancer of the gastrointestinal tract, skin cancer and mammary gland cancer have been examined.

We claim:

1. A method for diagnosing malignant neoplasms in a patient which comprises administering to said patient a diagnostically effective amount of a contrasting agent consisting essentially of, in percent by weight of the total contrasting agent, from about 0.1 to about 80 percent of fluorescein or salts thereof, and from about 20 to about 99.9 percent of at least one sugar for increasing the fluorescein concentration in malignant neoplasms and thereafter detecting the location of said contrasting agent in said patient.

2. The method of claim 1 wherein said fluorescein salts are ammonium salts.

3. The method of claim 1 wherein said fluorescein salts are alkali metal salts.

4. The method of claim 3 wherein said alkalai metals are selected from the group consisting of lithium, sodium, and potassium.

5. The method of claim 1 wherein said sugar is at least one member selected from the group consisting of glucose and fructose.

6. The method of claim 5 wherein said sugar is glucose.

7. The method of claim 5 wherein said sugar is fructose.

8. The method of claim 1 wherein the contrasting agent is contained in an inert carrier in the form of a powder, solution and/or mixture thereof.

9. The method of claim 1 wherein the contrasting agent is contained in an inert carrier in the form of an aqueous solution.

10. The method of claim 1 wherein the contrasting agent is contained in an inert carrier in the form of an aqueous-alcohol solution containing from about 5 to 30 weight percent alcohol.

* * * * *